US006179790B1

(12) United States Patent
Cundari et al.

(10) Patent No.: US 6,179,790 B1
(45) Date of Patent: Jan. 30, 2001

(54) LAYER OF MATERIAL FOR USE WITH TISSUE EXAMINATION DEVICE

(75) Inventors: Michael Anthony Cundari, Hingham; Alan Irving West, Hopkinton; Troy William Roberts, Pepperell, all of MA (US)

(73) Assignee: Assurance Medical, Inc., Hopkinton, MA (US)

( * ) Notice: Under 35 U.S.C. 154(b), the term of this patent shall be extended for 0 days.

(21) Appl. No.: 08/954,454

(22) Filed: Oct. 20, 1997

(51) Int. Cl.[7] .................................................. A61B 5/103
(52) U.S. Cl. ............................................ 600/587; 600/595
(58) Field of Search ..................................... 600/587, 592, 600/595

(56) References Cited

U.S. PATENT DOCUMENTS

| Re. 30,446 | 12/1980 | Meyers et al. ........................ 128/736 |
| Re. 32,000 | 10/1985 | Sagi ...................................... 128/736 |
| 3,154,789 | 11/1964 | Lewis, Jr. ................................ 2/104 |

(List continued on next page.)

FOREIGN PATENT DOCUMENTS

| PCT/US96/ 17173 | 10/1996 | (EP) . |
| 2 086 575 | 5/1982 | (GB) . |

OTHER PUBLICATIONS

Sarvazyan, A., "Knowledge–Based Mechanical Imaging of the Prostate", Medical Technologies & Programs A forcast for the future, pp. 87–94, Aug. 14–17.

Sarvazyan, A. , "Knowledge–Based Mechanical Imaging", Tenth IEEE Symposium on Computer–Based Medical Systems, pp. 120–125, Jun. 11–13, 1997.

E.J. Chen et al., "Ultrasound Tissue Displacement Imaging with Application to Breast Cancer", 1995, Ultrasound in Med. & Biol., vol. 21, No. 9, pp. 1153–1156, Michigan, U.S.A.

R.S. Fearing et al., "A Tactile Sensing Finger Tip for a Dextrous Hand", Oct. 1986, 5th SPIE Intelligent Robotics and Computer Vision, pp. 1–10, Cambridge, Massachusetts.

Brian S. Garra, et al. "Elastography of Breast Lesions: Initial Clinical Results" 1997, Radiology, vol. 202, pp. 69–86.

F. Kallel et al., "Fundamental Limitations on the Contrast–Transfer Efficiency in Elastography: an Analytic Study", 1996, Ultrasound in Med. & Biol., vol. 22, No. 4, pp. 463–470.

Dr. Ricki Lewis, "New Imaging Technology May Detect Early Cancer", Biophotonics in Action, Oct. 1996, Photonics Spectra, pp. 52–53.

G. Piperno et al., "Breast Cancer Screening by Impedance Measurements", 1990, Frontiers Med. Biol. Engng. vol. 2, No. 2, pp. 111–117.

(List continued on next page.)

Primary Examiner—Max Hindenburg
Assistant Examiner—Pamela L. Wingood
(74) Attorney, Agent, or Firm—Fish & Richardson P.C.

(57) ABSTRACT

A layer of material is provided for covering a plurality of sensors when using those sensors to examine tissue. The layer material is used with a tissue examination device that has a plurality of pressure sensors that produce signals in response to pressure imposed on the sensor as the sensors are pressed against tissue. The device also has a processor for processing those signals to detect whether an underlying tissue structure is present in the tissue being examined. The layer of material is configured to be disposed over the sensors and to distribute the imposed pressure in a selected manner. The processor can also process the signals to generate an image representative of the underlying tissue structure and a display then can display that image.

67 Claims, 8 Drawing Sheets

U.S. PATENT DOCUMENTS

| | | |
|---|---|---|
| 3,308,476 | 3/1967 | Kleesattel . |
| 3,323,352 | 6/1967 | Branson . |
| 3,744,490 | 7/1973 | Fernandez ............................ 128/2.05 |
| 3,847,139 | 11/1974 | Flam ..................... 128/2 H |
| 3,854,471 | 12/1974 | Wild ..................... 128/2 V |
| 3,880,145 | 4/1975 | Blick ..................... 128/2.05 |
| 3,970,862 | 7/1976 | Edelman et al. .................. 307/88 ET |
| 3,972,227 | 8/1976 | Tomilov ............................. 73/67.7 |
| 3,996,922 | 12/1976 | Basham ............................. 128/2 R |
| 4,001,951 | 1/1977 | Fasse ......................................... 35/17 |
| 4,023,562 | 5/1977 | Hynecek et al. ................. 128/2.05 E |
| 4,025,165 | 5/1977 | Sollish et al. ...................... 350/161 S |
| 4,132,224 | 1/1979 | Randolph ............................. 128/2 S |
| 4,134,218 | 1/1979 | Adams et al. ............................ 35/17 |
| 4,135,497 | 1/1979 | Meyers et al. ....................... 128/2 H |
| 4,144,877 | 3/1979 | Frei et al. ............................. 128/2 S |
| 4,159,640 | 7/1979 | Leveque et al. ............................ 73/81 |
| 4,190,058 | 2/1980 | Sagi ..................... 128/736 |
| 4,212,306 | 7/1980 | Mahmud ............................. 128/665 |
| 4,219,708 | 8/1980 | Rubey ............................. 200/61.47 |
| 4,250,894 | 2/1981 | Frei et al. ............................. 128/774 |
| 4,286,602 | 9/1981 | Guy ..................... 128/665 |
| 4,291,708 | 9/1981 | Frei et al. ............................. 128/734 |
| 4,346,717 | 8/1982 | Haerten ................................. 600/461 |
| 4,458,694 | 7/1984 | Sollish et al. ......................... 128/734 |
| 4,503,865 | 3/1985 | Shishido ............................... 128/774 |
| 4,524,778 | 6/1985 | Brown, Jr. et al. .................... 128/736 |
| 4,555,953 | 12/1985 | Dario et al. ......................... 73/862.04 |
| 4,570,638 | 2/1986 | Stoddart et al. ....................... 128/665 |
| 4,600,011 | 7/1986 | Watmough ............................. 128/664 |
| 4,641,659 | 2/1987 | Sepponen ............................. 128/653 |
| 4,641,661 | 2/1987 | Kalarickal ............................. 128/744 |
| 4,651,749 | 3/1987 | Sagi ..................... 128/736 |
| 4,657,021 | 4/1987 | Perry et al. ........................... 128/630 |
| 4,729,378 | 3/1988 | Trittenbass ............................. 128/645 |
| 4,737,109 | 4/1988 | Abramson ............................. 434/267 |
| 4,768,516 | 9/1988 | Stoddart et al. ....................... 128/665 |
| 4,774,961 | 10/1988 | Carr ..................... 128/736 |
| 4,790,329 | 12/1988 | Simon ............................. 128/749 |
| 4,793,354 | 12/1988 | Wright et al. ......................... 128/630 |
| 4,807,637 | 2/1989 | Bjorkhom ............................. 128/664 |
| 4,810,875 | 3/1989 | Wyatt ..................... 250/227 |
| 4,817,623 | 4/1989 | Stoddart et al. ....................... 128/665 |
| 4,873,982 | 10/1989 | Morrison ............................. 128/630 |
| 4,886,070 | 12/1989 | Demarest ............................. 128/675 |
| 5,005,581 | 4/1991 | Honeyager ............................. 600/461 |
| 5,010,772 | 4/1991 | Bourland et al. ................. 73/862.04 |
| 5,012,817 | 5/1991 | Zeilinski et al. ...................... 128/744 |
| 5,031,634 | 7/1991 | Simon ................................. 128/754 |
| 5,079,698 | 1/1992 | Grenier et al. .................. 364/413.13 |
| 5,099,848 | 3/1992 | Parker et al. .................... 128/661.07 |
| 5,140,989 | 8/1992 | Lewis et al. ......................... 128/665 |
| 5,143,079 | 9/1992 | Frei et al. ............................. 128/734 |
| 5,212,637 | 5/1993 | Saxena ........................... 364/413.26 |
| 5,221,269 | 6/1993 | Miller et al. ......................... 604/281 |
| 5,265,612 | 11/1993 | Sarvazyan et al. ............. 128/660.01 |
| 5,273,046 | 12/1993 | Butterfield ........................... 600/485 |
| 5,301,681 | 4/1994 | DeBan et al. ......................... 128/736 |
| 5,301,682 | 4/1994 | Debbas ................................. 128/737 |
| 5,333,612 | 8/1994 | Wild ................................. 128/660.9 |
| 5,363,852 | 11/1994 | Sharkawy ............................. 600/461 |
| 5,511,561 | * 4/1996 | Wanderman et al. ................ 600/592 |
| 5,524,636 | 6/1996 | Sarvazyan et al. ............... 128/660.9 |
| 5,678,565 | 10/1997 | Sarvazyan ............................. 128/774 |
| 5,785,663 | 7/1998 | Sarvazyan ............................. 600/587 |
| 5,795,308 | 8/1998 | Russin ................................. 600/567 |
| 5,807,276 | 9/1998 | Russin ................................. 600/567 |
| 5,833,634 | 11/1998 | Laird et al. ........................... 600/587 |

OTHER PUBLICATIONS

G.I. Pressman et al., "A Transducer for the Continuous External Measurement of Arterial Blood Pressure", 1960s, IEEE Transactions on Bio–Medical Electronics.

Martin Feder et al., "Transducer Characteristics for Ultrasonic Stereoholography", Dec. 1976, Bull. N.Y. Acad. Med., vol. 52, No. 10, pp. 1207–1223.

B.D. Sollish et al., "Microprocessor–Assisted Screening Techniques", 1981, Israel J. Med. Sci., pp. 859–864, Israel.

R.G. Stevens et al., "The use of Difference of Gaussian Image Filtering to Assess Objectively the Correlations Between Breast Vascularity and Breast Cancer", 1988, Phys. Med. Biol., vol. 33, No. 12, pp. 1417–1431, U.K.

* cited by examiner

LAYER OF MATERIAL FOR USE WITH TISSUE EXAMINATION DEVICE

BACKGROUND

This invention relates to examining tissue with pressure sensors.

All women are at risk for breast cancer. This risk increases as a woman ages. Women are generally considered to be at increased risk for developing breast cancer if they have one or more of the following risk factors: a family history of breast cancer, a previous diagnosis of a malignant breast tumor or other gynecological cancers, hormonal factors, or not having had any children or having a first child later in their child bearing years. Even so, the majority of all breast cancers occur in women who apparently do not have identifiable risk factors.

Although breast cancer currently cannot be prevented, it can be detected at an early, treatable stage when the tumor is small and has not spread beyond the breast. Women who are treated at this early stage have a much higher survival rate than women who are treated at more advanced stages of the disease. However, not all breast cancers are currently detected at this early stage. Therefore, the importance of screening for breast cancer has become a critical a aspect in the overall management of this disease.

The methods currently used in the United States to screen for breast cancer and other breast conditions include monthly Breast self examination (BSE), mammography, and clinical breast examination.

Breast self examination is manual examination of a woman's breast tissue by the woman herself. During such examinations, a woman should examine her breasts at the same time each month, 7–10 days after the first day of her last menstrual cycle. She should report to her physician anything she feels that is new or that has changed since her prior exam.

Breast self examinations are important for the early detection of breast cancer. However, many women do not perform these examinations. When questioned about this, most women explain that they are not comfortable with their level of skill in doing such examinations. Products which help to remove the obstacles that prevent women from examining their breasts regularly would clearly be beneficial. Ideally, these products would increase the quality of such examinations without requiring extensive technical skill from their users.

Several devices designed to assist the user and clinicians in performing breast self examination are described in commonly-owned U.S. patent application Ser. No. 08/757,466, entitled "Tissue Examination" (hereinafter, "the '466 application), incorporated herein by reference. These devices include an array of sensors each of which produces a signal in response to the pressure imposed thereon as the sensor is pressed against tissue. The pressure varies in accordance with properties of different types of underlying tissue structures. Processing tests are performed on the signals to discern the characteristics of underlying tissue structures and thus discriminate between different types of underlying tissue (e.g., potentially foreign structures such as cysts or solid masses, and normal structures such as a nipple, a rib, or a ligament). Accordingly, the devices can alert the user to the presence of suspicious or indeterminate discrete and dominate structures in breast tissue.

Many of the processing tests performed by the devices described in the '466 application search for small differentials in the outputs of the pressure sensors. Random or patterned faults, due e.g. to surface abrasions or small tissue structures near the surface, may produce erroneous test results, thereby potentially leading to "false positive" indications of potentially foreign tissue structures. Moreover, if some of the sensors respond unduly weakly to imposed pressure, due e.g. to sensors being damaged, the device may fail to detect an underlying structure (particularly if the weakened sensors are concentrated together in the array).

SUMMARY

This invention concerns examining a tissue using pressure sensors and disposing a layer of material on the sensors during examination. In one general aspect, the invention features an apparatus that includes a tissue examination device and a layer of material. The tissue examination device has a plurality of pressure sensors that produce signals in response to pressure imposed on the sensors as the sensors are pressed against tissue. The device also has a processor for processing those signals to detect whether an underlying tissue structure is present in the tissue being examined. The layer of material is configured to be disposed over the sensors and to distribute the imposed pressure in a selected manner.

In another general aspect, the invention features an apparatus that includes a tissue examination device and a layer of material. The tissue examination device has a plurality of pressure sensors that produce signals in response to pressure imposed on the sensors as the sensors are pressed against tissue. The device also has a processor for processing the signals to generate an image representative of the underlying tissue structure, and a display for displaying that image. The layer of material is configured to be disposed over the sensors and to distribute the imposed pressure in a selected manner.

In yet another general aspect, the invention features a layer of material to be used with a tissue examination device. The tissue examination device has a plurality of pressure sensors that produce signals in response to pressure imposed on the sensors as the sensors are pressed against tissue. The device also has a processor for processing those signals to detect whether an underlying tissue structure is present in the tissue being examined. The layer of material is configured to be disposed over the sensors and to distribute the imposed pressure in a selected manner.

In another general aspect, the invention features a layer of material to be used with a tissue examination device. The tissue examination device has a plurality of pressure sensors that produce signals in response to pressure imposed on the sensors as the sensors are pressed against tissue. The device also has a processor for processing the signals to generate an image representative of the underlying tissue structure, and a display for displaying that image. The layer of material is configured to be disposed over the sensors and to distribute the imposed pressure in a selected manner.

In another aspect, the invention relates to a method of examining tissue. A tissue examination device is provided. The tissue examination device includes a plurality of pressure sensors that produce signals in response to pressure imposed on the sensors as the sensors are pressed against tissue. A layer of material is disposed over the sensors to distribute the imposed pressure in a selected manner. The sensors are then pressed against the tissue to examine the tissue.

Preferred embodiments may include one or more of the following features.

The layer of material distributes the pressure imposed on a sensor to an adjacent sensor, which may be one of the surrounding sensors. The sensors can have a top layer and the layer of material is configured to reduce a deflection of the top layer in response to the imposed pressure.

The imposed pressure is shear stress imposed by the tissue on the sensors when the sensors are moved over the tissue. In that case, the layer of material distributes the shear stress to reduce the shear stress imposed on the sensors. The sensors can have a top and a bottom layer, the top layer being capable of moving relative to the bottom layer in response to the shear stress. The layer of material is configured to reduce a movement of the top layer relative to the bottom layer caused by the shear stress. A lubricant is disposed between the top layer of the sensors and the layer of material which can assist with reducing the movement of the top layer relative to the bottom layer.

The tissue examination device has a housing which is made up of a sensor head on which the sensors are installed and a neck connected to the sensor head. The layer of material distributes the stress imposed on the layer of material to the housing to reduce the shear stress on the sensors. The layer of material is attached to the housing and covers the sensor head. The layer of material may be a sheath configured to be attached to housing by frictionally engaging, or adhesively attaching to, the neck.

The layer of material is constructed from a material selected for distributing pressure imposed on one of the sensors to surrounding sensors. The selected material may be polyurethane having a thickness of 0.001–0.005 inch. The layer of material may also be constructed from a material selected for operating with a selected lubricant.

The layer may be permanently attached to the housing or may be attached temporarily to the housing by a user and disposed of after use.

Advantages of the invention may include one or more of the following advantages.

The layer of material according to this invention distributes the pressure so as to assist a tissue examination device or a clinician using a tissue examination device to filter out small structures on or near the surface. Therefore, the layer of material reduces the number of false positive detections or non-detection by the tissue examination device or a clinician analyzing images based on the pressure signals from the sensors.

The layer of material also distributes shear stress away form the sensors to protect the sensors against being damaged by such stress and therefore increase the life of the sensors and maintain their accuracy.

The layer of material also protects the sensors against impact, which may result for example from dropping the device, and which tends to damage the sensors and reduce the accuracy of the sensors.

Embodiments of the device can be in the form of disposable sheaths and assist with improving hygiene, especially in clinical tissue examination settings where there is increased risk of communicable diseases.

Material selected for constructing embodiments of the layer can be selected based on their interaction with selected lubricants to provide optimal lubrication during tissue examination which assists with the examination and enhances the results from the examination.

DESCRIPTION

Figure 1:
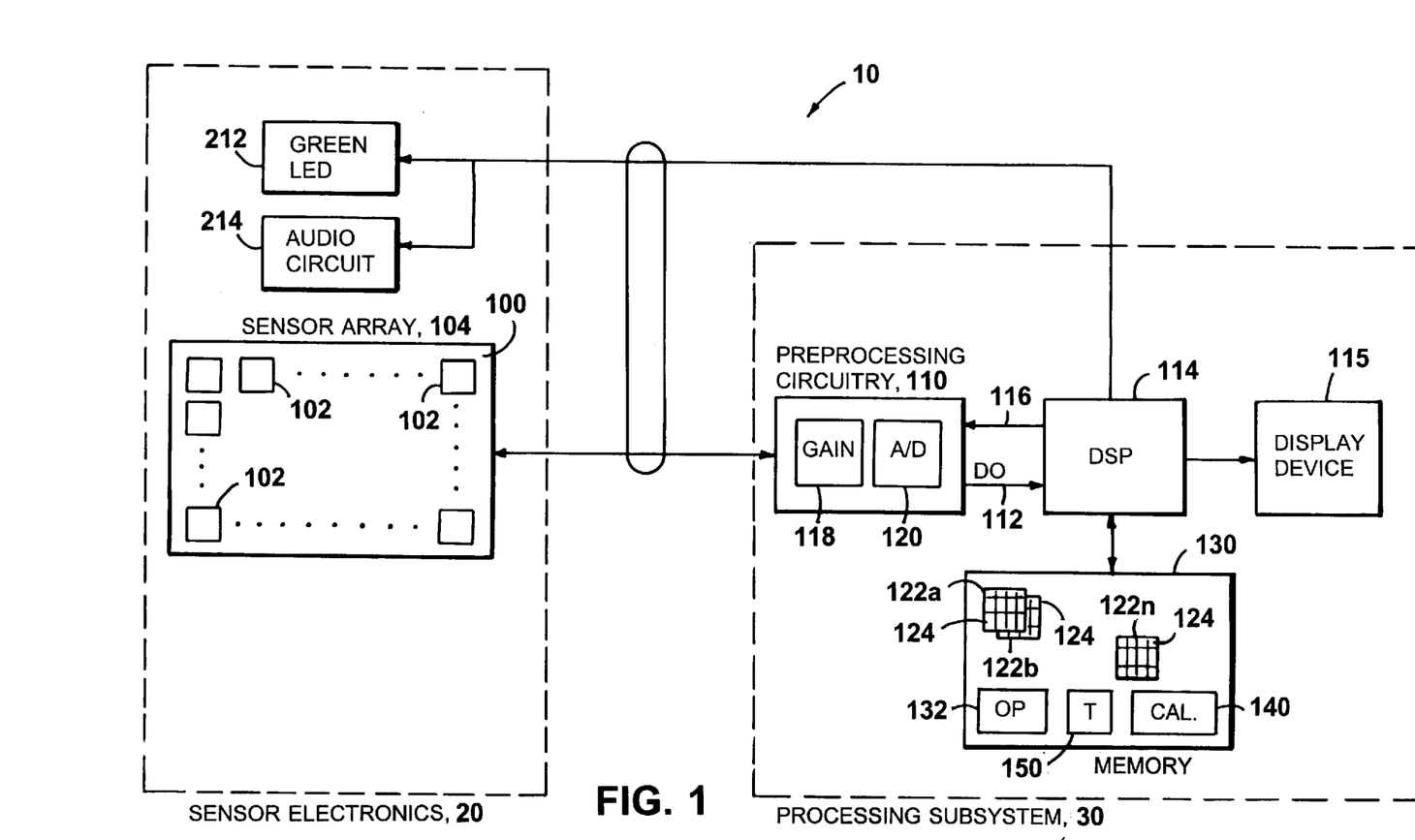
FIG. 1 is a block diagram of a tissue examination device having an array of pressure sensors.
Figure 2:
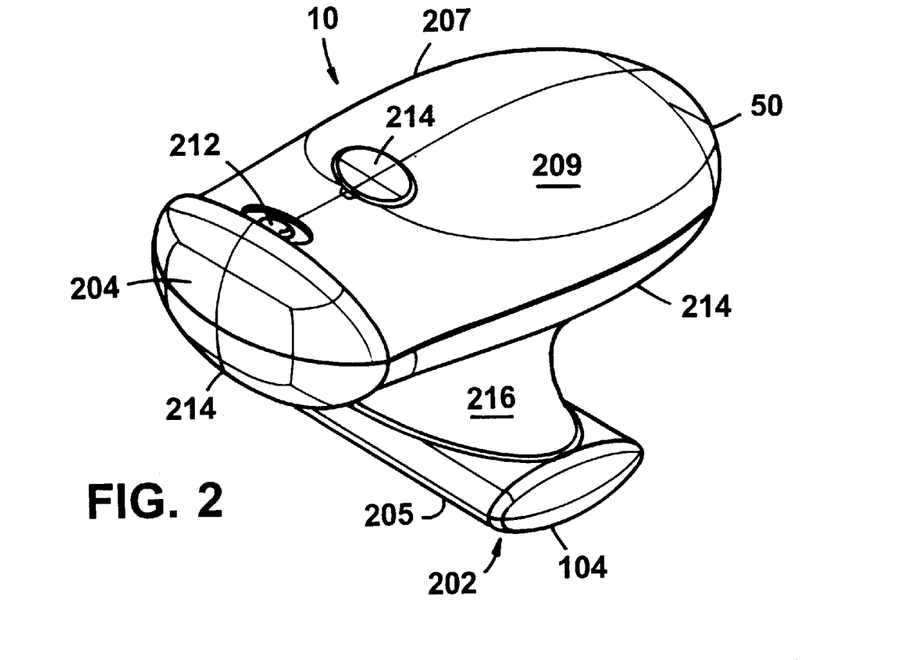
FIGS. 2 and 2A are perspective views of the tissue examination device.
Figure 2A:
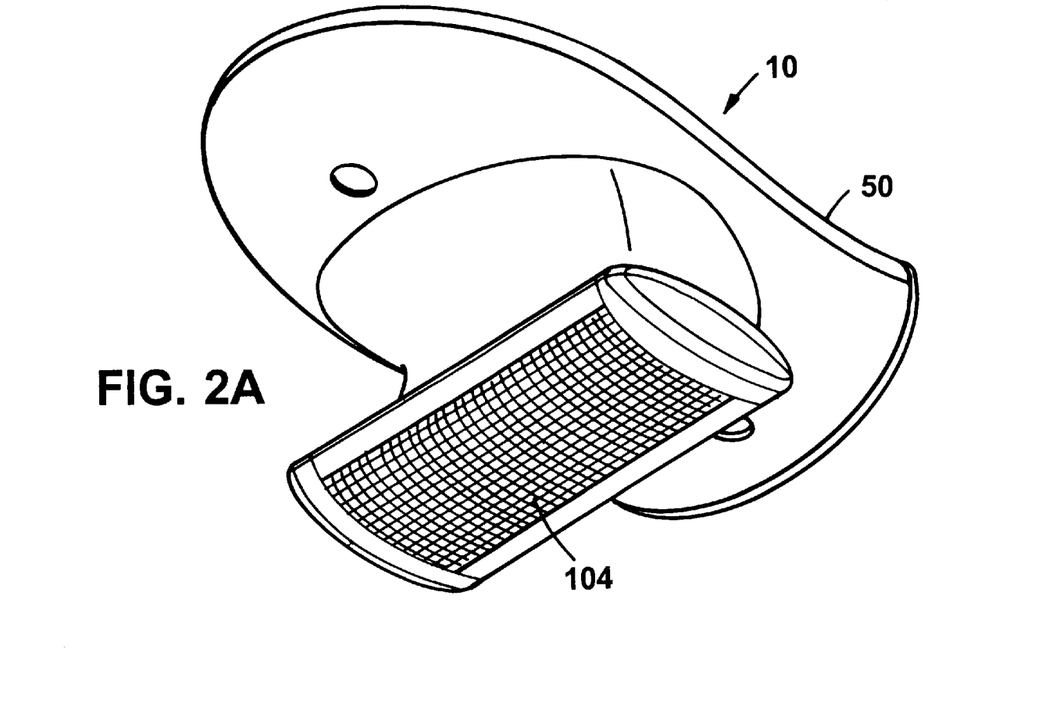

Referring to FIGS. 1 and 2–2A, tissue examination device 10 includes sensor electronics 20 connected to a processing subsystem 30 via a cable 40, all of which are mounted in a housing 50. As described in the '466 application, sensor electronics 20 include an array 104 of pressure sensors 102 carried on a thin, flexible membrane 100. Array 104 is, for example, a contact sensor such as that described in U.S. Pat. No. 4,856,993, entitled "Pressure and Contact Sensor System for Measuring Dental Occlusion" (the '993 patent), incorporated herein by reference, the individual pressure sensors 102 of which are resistive elements. Pressure sensors 103 are arranged in an orthogonal grid of rows and columns in array 104. Pressure sensors 102 are relatively small and are closely spaced to provide high resolution capable of distinguishing between areas of underlying tissue separated by 1 mm or less. Array 104 is commercially available from Tekscan, Inc. (the assignee of the '993 patent).

Housing 50 comprises an integral sensor head 202 and handle 204 made from a rigid polymer such as polycarbonate. Sensor array 104 is mounted on a lower surface 205 of head 202, with sensors 102 being exposed beneath head 202 for contacting the tissue. Lower surface 205 is convex, with a radius of curvature of approximately 1.5 inches to enhance the mechanical coupling between sensors 102 and the underlying tissue. The mechanical coupling can also be improved by lubricating the tissue to be examined (e.g., the breast) with a suitable lubricating agent, such as a gel. In use, the user grasps handle 204 and presses sensor head 202 against the breast and manually moves head 202 across the lubricated skin to translate sensor array 104 over the tissue. The translation technique is essentially a series of stationary palpations which allow the user to increase breast area coverage with less exam time.

Handle 204 is shaped to be conveniently grasped by a user to comfortably place array 104 against the breast, and the longitudinal axis of handle 204 is orthogonal to that of head 202. Specifically, the side surfaces 207 and upper surface 209 of handle 204 are curved as shown to allow handle 204 to be held in the palm of the hand with the longitudinal axis of head 202 arranged generally in the same direction as the user's forearm. This allows the user to maintain sensor head 202 (and hence sensor array 104) against the breast during the examination without bending or otherwise straining the wrist.

The underside 214 of handle 204 smoothly meets a tapered neck 216 which connects handle 204 to sensor head 202. The surfaces of neck 216 are also curved to allow for easy manipulation by the user.

The resistance of each pressure sensor 102 changes in accordance with the amount of pressure applied to sensor 102. The resistance change is inversely proportional to the pressure imposed on sensor 102. Thus, the resistance of each sensor 102 decreases as applied pressure increases. Generally, the pressure imposed on sensors 102 increases when sensors 102 are pressed against localized areas of stiffer tissue on, within, or below the softer breast tissue. Examples of such stiffer tissue include normal breast tissue structures—such as the nipple, the inframammary ligament, and underlying ribs—and foreign bodies such as cysts and solid masses (whether or not pathogenic). Consequently, as array 104 is pressed and moved against the breast, the pressure imposed on sensors 102 and, thus their resistance, varies in accordance with the properties of the underlying tissue structures.

The individual resistances of pressure sensors 102 are read by preprocessing circuitry 110 (FIG. 1), which produces corresponding digital output (DO) signals 112 that are applied to a digital signal processor (DSP) 114. Briefly, preprocessing circuitry 110 sequentially measures the resistance of pressure sensors 102 in response to row and column address signals 116 provided by DSP 114 to provide an indication of pressure applied to the location in array 104 that corresponds to that sensor 102. During each resistance measurement, preprocessing circuitry 110 applies a reference potential (not shown) to the addressed sensor 102 and measures the resulting voltage drop induced across that sensor 102. Preprocessing circuitry amplifies this voltage in gain stage 118 to scale the measured voltage drop to desired levels.

The amplified voltage levels are then digitized by A/D converter 120 to produce the digital output (DO) signals 112 the values of which correspond to the resistance-induced voltage drops. (Alternatively, DSP 114 can perform the digitization.) In this way, each pressure sensor 102 produces a DO signal 112 having a digital value that represents the pressure applied to that sensor 102. The operation of preprocessing circuitry 110 is more fully described in the '993 patent.

The set of sequentially produced DO signals 112 for all pressure sensors 102 in array 104 is termed a "frame." DSP 114 addresses preprocessing circuitry 110 at a rate sufficient to read 8 frames or more of DO signals 112 per second. DSP 110 stores each frame of DO signals 112 in an area 122a–122i of memory 130. Each memory area 122a–122i contains storage locations 124 which respectively correspond to the locations of pressure sensors 102 in array 104. Thus, each memory area 122a–122i contains a "map" of the pressures detected by pressure sensors 102 in a frame. This map can be viewed as a "pressure signature" of the tissue structures beneath array 104. Accordingly, memory areas 122a–122i contain a time sequence of pressure signatures of the underlying tissue as array 104 is palpated across the breast.

Figure 10:
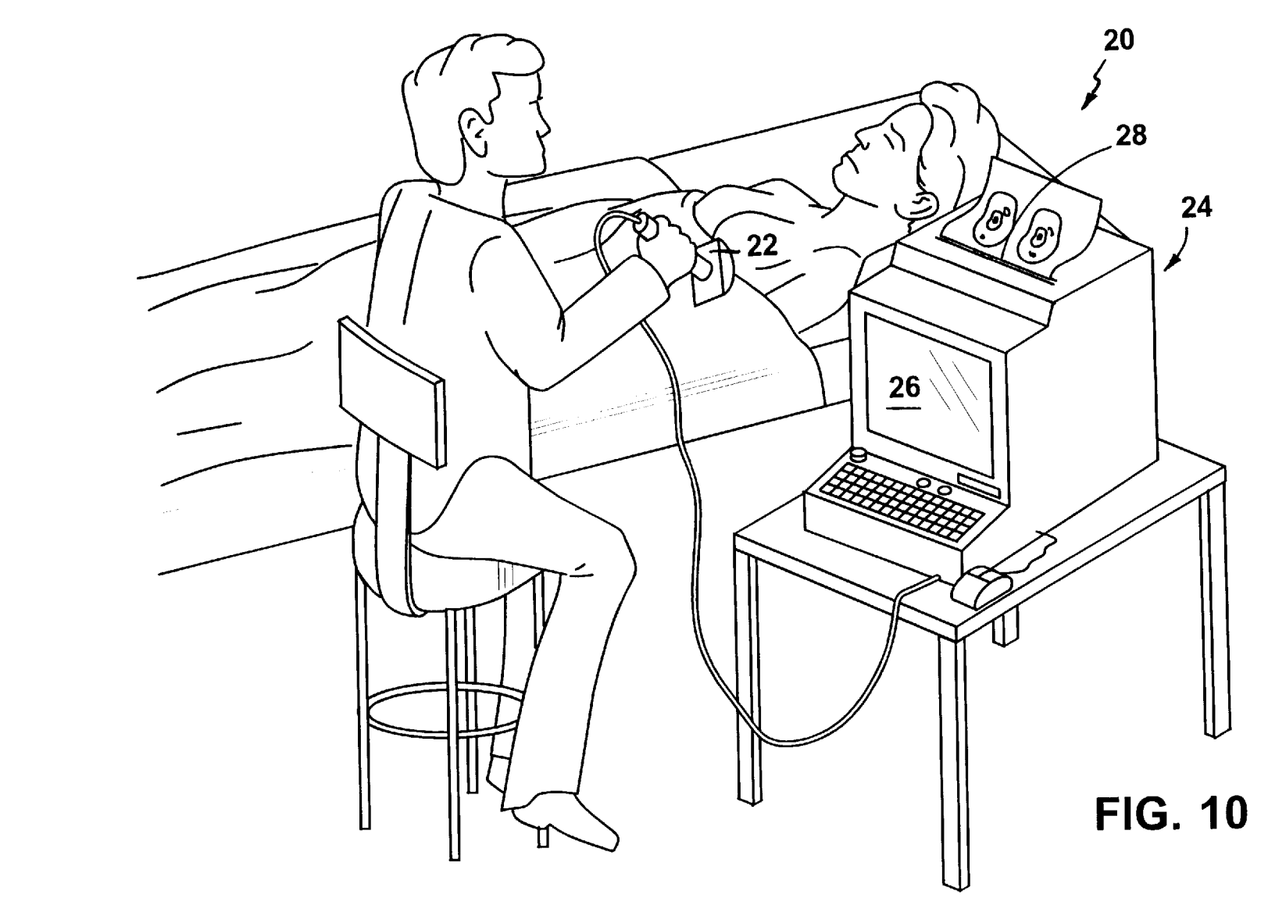
FIG. 10 shows a clinical tissue examination device.

Housing 50 may also include a communication port (not shown) for coupling the maps of the array of DO signals 112 to a display device 115, thereby allowing the user to observe the pressure signatures directly. DSP 114 may also display the pressure signatures as images on display device 115 in a variety of ways, as described in commonly owned patent application entitled "Clinical Tissue Examination," Ser. No. 08/931,573, filed on Sep. 16, 1997 (hereinafter, "the '573 application"), which is incorporated herein by reference. FIG. 10 shows an embodiment 20 of device 10 as configured according to the '573 patent application. That embodiment will be described briefly below and is described in detail in the '573 application.

The device described in the '573 application displays a 3 dimensional image of the pressure signatures of the tissue underlying sensors 102. The displayed three dimensional image is a graphical representation of the pressure readings from the array of sensors. First and second dimensions of the image represent the location of sensors 102 in the array, while the third dimension represents the pressure readings of sensors 102 and may be displayed with a color scale that corresponds to the pressure on sensors 102. The '573 application's device can display a plan view or a perspective view of this three dimensional image. In this image, the pressure signatures of the various underlying tissue structures appear to have various shapes whose characteristics are based on the type of underlying tissue structure. Therefore, a clinician can readily identify the underlying tissue structure by analyzing these shapes and their characteristics. DSP 114 may also perform additional processing to enhance the displayed images and provide further discrimination, as described in the '573 application.

As described in the '466 application, different types of tissue structures have different pressure signatures which can be used to differentiate the tissue structure types from each other. The pressure signatures result from the way in which the tissue structures respond to being stressed by the pressures exerted when the user moves array 102 over the breast. The stiffness (elasticity) of a given tissue structure, its composition (e.g., percentage of fat, presence of ducts, and fibrous tissue), its density, and the degree to which the tissue structure is held in place by surrounding tissue are all factors that contribute to the pressure signature of the tissue structure. Another factor which affects the resulting pressure signature is whether anatomical structures (e.g. ribs) lie beneath the tissue structure. These factors, in combination, are sufficiently different for various types of tissue structures (e.g., normal breast structures such as ribs, nipples, ligaments, etc., and foreign structures such as cysts, solid masses, and other lumps with respect to normal tissue stiffness) that the pressure signatures of these structures are distinguishable from each other.

DSP 114 performs various processing tests (described in detail in, e.g., the '466 application) defined by an operating program (OP) 132 stored in memory 130 on the pressure signatures stored in memory areas 122a–122i. The tests enable DSP 114 to discriminate normal underlying tissue structures from potentially foreign structures. If DSP 114 determines a potentially foreign tissue structure is present, DSP 114 notifies the user by sounding an alarm (e.g., a high-pitched tone) using an audio circuit 214 in handle 204 (FIGS. 1 and 2–2A). A green LED 212 is illuminated when tissue examination device is powered on and calibrated, as described below.

As discussed above, the pressure signatures are a function of the amount of average pressure applied to sensors 102 when the user presses array 104 against the body. Thus, the pressure applied by the user should be within a selected range in order for the pressure signatures to accurately correspond to the various tissue structure types. The limits of the pressure range are a function of the maximum expected peak of a detected underlying tissue structure when the average pressure measured by sensors 102 is within the tone range described herein. For array 104 discussed above, the range of pressures to be measured by sensors 102 is 0 psi to 5 psi.

Because the proper amount of user-applied pressure is important, DSP 114 examines each frame to determine whether the average amount of pressure applied to all sensors 102 is within an acceptable range (e.g., 0.5 psi to 2.0 psi). DSP 114 also determines if a minimum number of sensors 102 are obtaining a reading across width of array 104 such that DSP 114 recognizes that entire array 104 is in contact with the skin. If the frame fails either of these inquiries (e.g., if the user is applying an incorrect amount of pressure to the tissue with device 10), the frame is considered invalid and is not examined further in the test procedure. Otherwise, DSP 114 triggers audio circuit 214 to produce a low pitched humming tone. DSP 114 maintains this tone throughout the tissue examination (as long as the user is applying pressure within the correct range) to give the user feedback that the applied pressure is correct.

The various processing tests and other procedures performed by DSP 114 on output signals 112 are described in the above-referenced applications and will not be repeated here. The accuracy of these tests and procedures—and thus the reliability of the feedback given (e.g., by audio circuit 214) to the user as to the presence or absence of a potentially foreign underlying structure in the tissue—is dependent on the accuracy of the signals produced by pressure sensors 102.

We have identified several potential sources of errors in the signals produced by sensors 102. Briefly, a first source of error is the presence of small areas of stiffness on or near the surface of the tissue which apply localized pressure to sensors 102. A second source of error is the damage to sensors that can be caused over time from shear stress (i.e. shear force or load) on sensors 102. A third source of error is the effect of physical impact on sensors 102. A user of device 10 may during normal use cause array 104 to be impacted by force, for example, as a result of accidently dropping device 10 onto a floor.

To reduce the effects of the above sources of errors, we have developed a layer of material for covering sensors 102. The layer of material may take the form of a sheath, as in sheath 300 in FIGS. 3 and 3A. Briefly, sheath 300 distributes the pressure applied to sensors 102 in a selected manner, so as to perform two functions: first, sheath 300 filters out small areas of localized pressure; and second, sheath 300 reduces shear stress on sensors 102. To perform the first function, sheath 300 distributes pressure imposed on a sensor to the sensor's adjacent or neighboring sensors. To perform the second function, sheath 300 distributes the shear stress away from array 104 and to housing 50. Moreover, sheath 300 provides a layer for protection against impact on array 104 and reduces the effects of such impacts.

We will now describe in detail the first two sources of errors and briefly indicate how sheath 300 assists with overcoming errors from these sources.

As mentioned above, the first source of the errors we have identified is the presence of small areas of stiffness on or near the surface of tissue. Generally, the tissue may have areas of increased stiffness or the skin may have surface aberrations or, at times, rough texture. The sizes of the areas of increased stiffness, the surface aberrations, or the features of a skin which has a rough texture may be small enough to apply localized pressure on individual sensors. The localized pressure can cause individual sensors to produce signal spikes. Since, the main goal of device 10 is to detect the stiffness of deeper and larger sized structures, these spikes are problematic noise and can have undesirable consequences in device 10. For example, these spikes can skew the results of the tests performed by device 10 such that device 10 may determine that there is a suspicious underlying structure where there is none. Similarly, these spikes can confuse a clinician analyzing images displayed by device 10 in accordance with the '573 application since the spikes appear as areas of high pressure. The spikes may therefore degrade the quality of the displayed images and result in the clinician falsely identifying a spike as a suspicious underlying structure or not identifying a suspicious underlying structure because of being misled or distracted by the spikes.

Briefly, sheath 300 filters out or reduces the effects of some, and preferably all, of these spikes. To do this filtering, sheath 300 distributes the pressure imposed by the tissue on a sensor to surrounding sensors. This distribution has the effect of dissipating localized pressure imposed by small structure on an individual sensors to that sensor's adjacent or surrounding sensors. This function of sheath 300 as will be described in more detail below.

The second source of error is the damage to sensors caused over time by shear stress on sensors 102 and by impact on sensors 102. Pressure sensors of the type according to the '993 patent typically have at least two layers, as will be described in detail below. A bottom layer is affixed to sensor head 202 by adhesive. A top layer is pressed against the tissue. As the device is translated across the tissue, the tissue applies a shear stress to the top layer. This shear stress pulls the top layer in the opposite direction of the movement of device 10 and the bottom layer. Even if a lubricant is used between the tissue and array 104, the tissue still applies a shear stress to array 104 in the opposite direction of the movement of array 104 over the tissue. Over time this type of shear stress may damage sensors 102 and reduce the accuracy of the sensor.

Briefly, sheath 300 distributes some, and preferably all, of the shear stress applied to the top layer of the sensor away from the top layer and prevents sensors 102 from being damaged. To do this, sheath 300 transfers the shear stress to housing 50. A dry lubricant between the layer of material and the top layer of sensors 102 further assists with sheath 300 transferring the shear stress away from sensors 102. This function of sheath 300 as will be described in more detail below.

We will now describe in detail the structure and operation of sheath 300 and how sheath 300 assists with overcoming the above sources of error. We will first describe the structure of sensors 102 and their operation to provide an appropriate context for describing sheath 300 and its operation. We will then describe the structure of sheath 300 and proceed to describe its operation in reference to the two ways in which it distributes pressured imposed on array 104.

Figure 4:
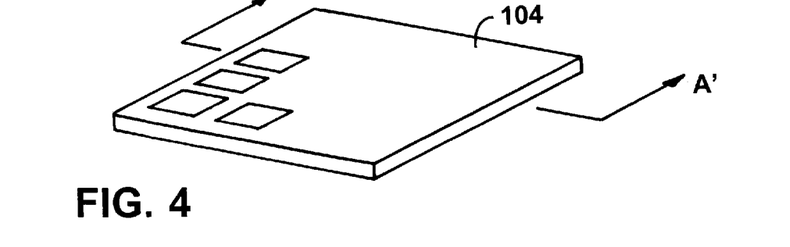
FIG. 4 shows an array of pressure sensors.
Figure 4A:
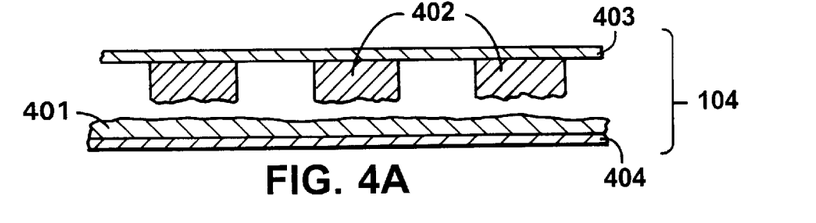
FIGS. 4A, 5A–5C, and 7 show partial cross-sections of the array of pressure sensors in FIG. 4 along A–A".

FIG. 4 shows array 104 and FIG. 4A shows a cross-section of array 104 along A–A'. (In FIG. 4a, only three sensors are shown; it will be understood that the number of sensors 102 in array 104 is typically much larger. Also, although array 104 is installed on a curved surface in device 10, we will show the operation of the structure and operation of array 104 in reference to a flatly installed embodiment of array 104 for simplifying the description of the operation of sheath 300. However, it should be understood that the same principles apply to embodiments in which array 104 is installed on a curved surface.) Array 104 has a top polymer layer 403 and a bottom polymer layer 404. Force Sensing Resistive (FSR) ink is deposited by screen printing on an area 401 on bottom layer 404 and on areas 402 on top layer 404. Each area 402 is a sensing location, i.e. a sensor. Array 104 is then constructed by top layer 403 being laid on bottom layer 404 and being bonded to bottom layer 404 on the perimeter.

During use, when pressure is applied to array 104, top layer 403 is pushed towards bottom layer 404. As the two layers near each other, the FSR ink on areas 402 of top layer 403 contacts the FSR ink on bottom layer 404. The higher the pressure on array 104 is, the more contact the FSR ink on the top and bottom layers make with one other and therefore the lower the resistance of sensors 102 becomes.

Figure 3:
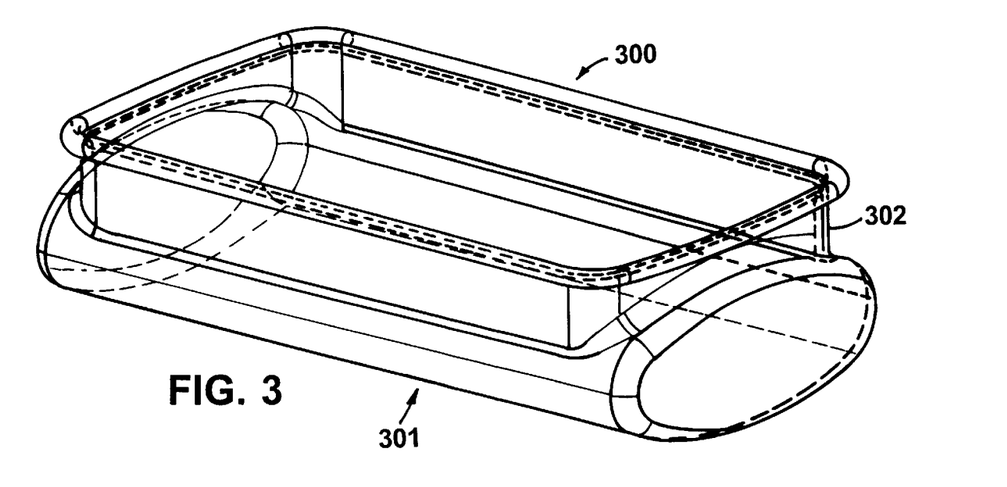
FIG. 3 is a perspective view of a sheath.
Figure 3A:
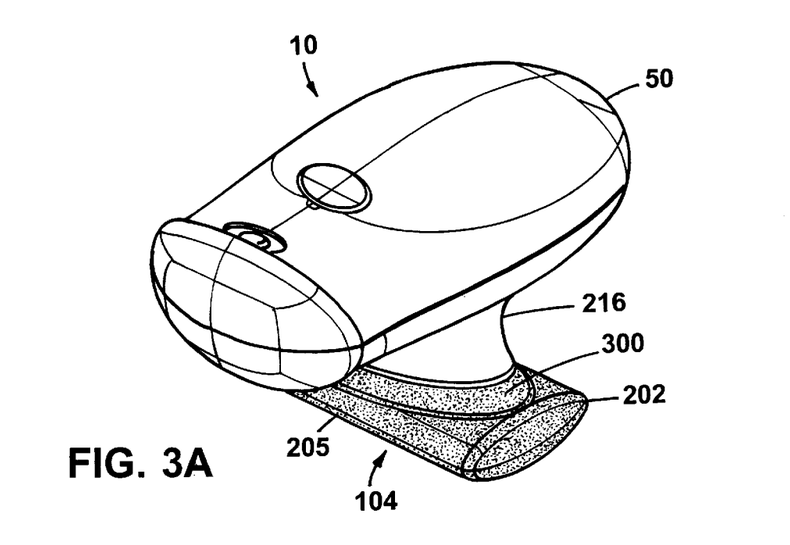
FIG. 3A is a perspective view of the tissue examination device with a sheath attached to it.

We will now describe, in reference to FIGS. 3 and 3A, an embodiment of sheath 300 for installation on device 10. Briefly, sheath 300 has two portions: a lower portion 301 and an upper portion 302. Lower portion 301 is designed to cover sensor head 202 of device 10. Upper portion 302 is designed to frictionally engage neck 216 of device 10.

The shape of lower portion 301 of sheath 300 follows the contour of the shape of sensor head 202. Sheath 300 is smaller in dimension than sensor head 202, preferably by approximately 10–25%, so that when sheath 300 is pulled over the sensor head it is slightly stretched over array 104. Sheath 300 size and material are selected to ensure that sheath 300 will not be too loose or too tight over array 104 surface. A sheath that is too loose could wrinkle or bunch over array 104 and cause the sensor array to produce signals which may appear as pressure signatures of suspicious underlying structures. Conversely, a sheath which is too tight can press against sensors 102 and cause them to "sense" pressure where none is applied to the surface of sensors 102.

The upper portion 302 is sized to ensure that significant stretching of the upper portion 302 over neck 216, preferably about 25%, will occur when sheath 300 is pulled over device 10. Effectively, undersizing sheath 300 results in sheath 300 being immobile relative to housing 50 when sheath 300 is pulled on to neck 216 and sheath 300 has frictionally engaged the neck.

In summary, sheath 300 is sized and configured relative to the size and shape of neck 216 and sensor head 202 to cause sheath 300 to grab firmly to housing 50 in the neck area but be only in smooth contact with the sensor area. In essence, sheath 300 is designed to have a selected tension around the neck of device 10 that is higher than a selected tension of sheath 300 on the sensor head.

A dry lubricant is used on the inner surface of sheath 300. This lubricant allows easy installation of sheath 300 onto housing 50. The lubricant also allows the movement of lower portion 301 of sheath 300 relative to array 104 so as to reduce shear stress on array 104, as will be described below.

We will now describe how sheath 300 filters out areas of localized pressure and reduces shear stress on sensors 102.

During operation, sheath 300 is pulled over sensor head 202. As described, during operation sheath 300 tightly grips neck 216 of device 10, while fits over sensors 102 such that it is suitably stretched. Lower potion 301 of sheath 300 essentially acts as an additional layer of elastic material over top layer 403 of array 104.

Figure 5A:
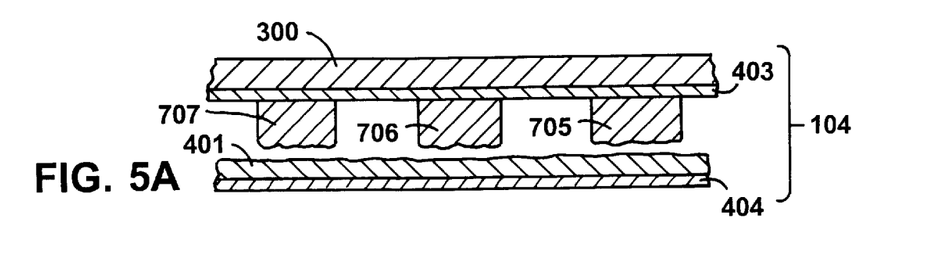
Figure 5B:
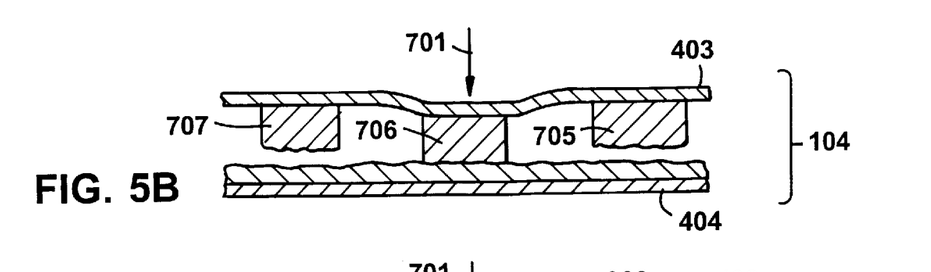
Figure 5C:
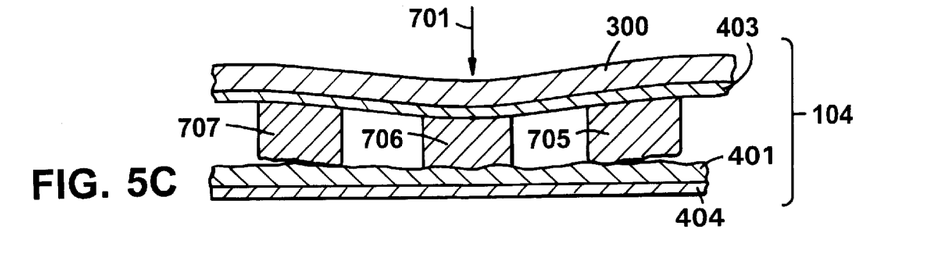

FIGS. 5A–5C show a cross-section of array 104, in particular three sensors 705, 706, 707. FIG. 5A illustrates sensors 705–707 when not pressed. FIGS. 5B and 5C illustrate situations where a localized pressure 701, such as a pressure that would be applied by areas of increased stiffness, surface aberrations, or rough skin texture may be small enough so as to contact a single sensor and cause a signal spike at that sensor. In FIG. 5B, sheath 300 does not cover array 104. When localized pressure 701 applied to sensors 706, the resistance of sensor 706 is proportionally lowered. An electrical signal produced by that sensor therefore will be proportional to that pressure. However, sensors 707 or 705 are not significantly affected by localized pressure 701. Therefore, their resistance is not significantly decreased and any electrical signal generated by them is therefore not significantly affected by localized pressure 701.

The fact that sensors 707 and 705 are not affected by localized pressure 701 indicates that array 104 has a high resolution and therefore can distinguish small pressure sources. However, such high resolution in device 10 may result in falsely identified, or unidentified, tissue structures because of signal spikes which are generated by sensors 102, as described above. When sheath 300 is present and localized pressure 701 is applied (FIG. 5C) to sensor 706, sheath 300 acts as a bridging beam between sensors 707, 705, and 706, resists deflection, and curves because of its beam like characteristic. Note that sheath 300's curvature is less than that of top layer 403 of array 104 without sheath 300. Therefore, sheath 300 distributes the localized pressure 701 to adjacent or surrounding sensors 707, 705. Sheath 300 also reduces the peak response of sensor 706. In effect, sheath 300 reduces the resolution of array 104.

Figures 6A, 6B:
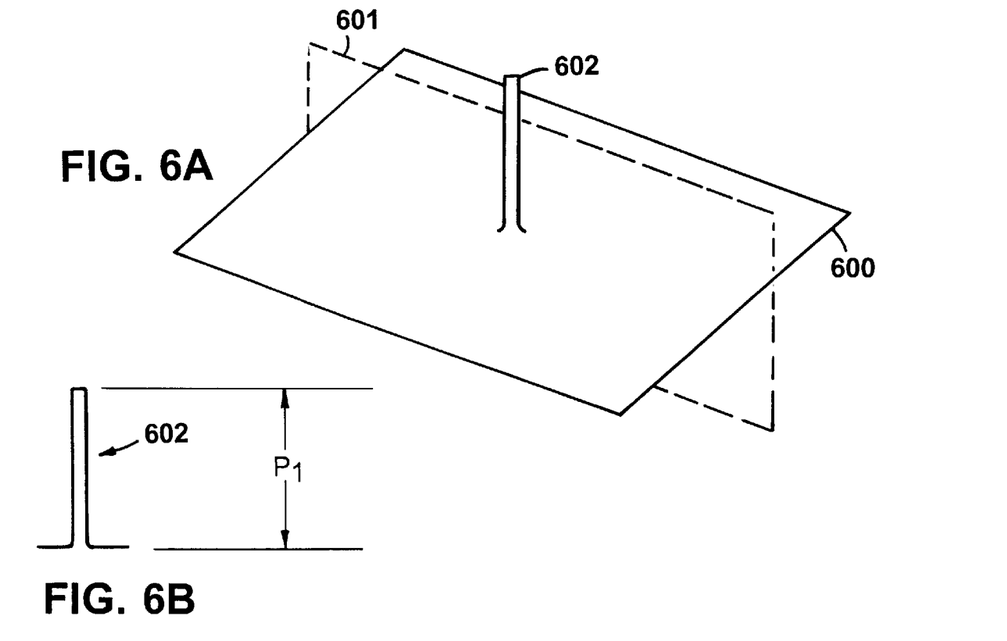
FIGS. 6A–6F show images of signals from an array of pressure sensors.
Figures 6C, 6D:
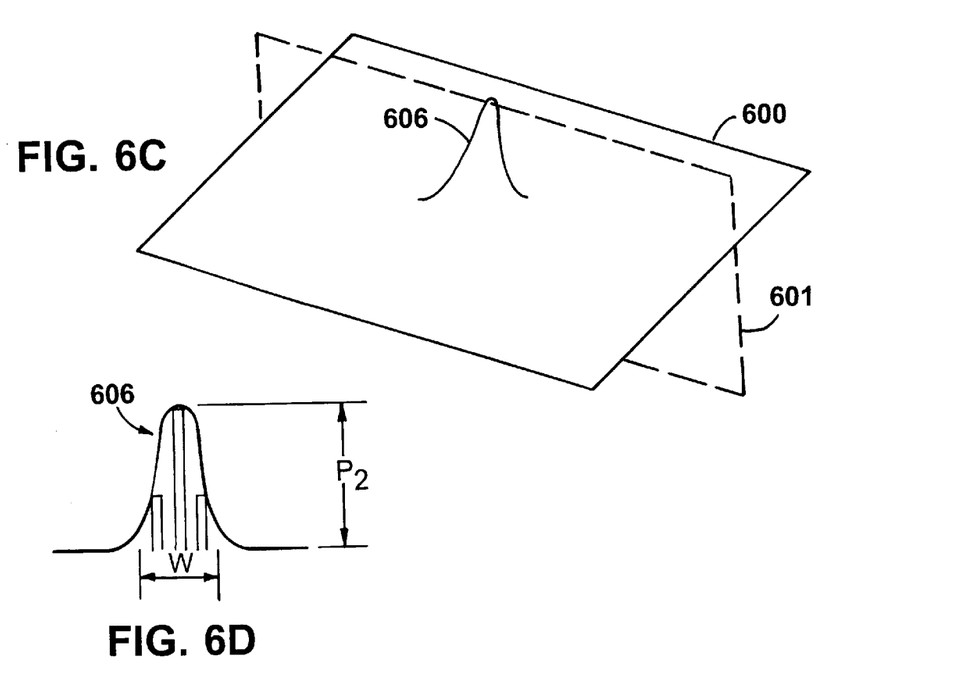

If the pressure signals from array 104 are displayed graphically, for example in accordance with the '573 application, the reduction in the peak pressure would be viewed as a drop in the height of a displayed pressure signature and the distribution of the applied pressure would be seen as an increase in the width of the displayed pressure signature. FIG. 6A shows a three dimensional image 602 of the signals generated by array 104 in response to a localized pressure when sheath 300 is not present. FIG. 6C shows a three dimensional image 606 of the signals generated by array 104 in response to a localized pressure when sheath 300 has distributed that pressure to adjacent or surrounding sensors. FIGS. 6B and 6D show cross-sections of images 602 and 606, respectively, along plane 601 which is coincident with the peak values of shapes 602 and 606 and parallel to the direction in which the sensor is pressed into the tissue. In FIGS. 6B and 6D, shapes 602 and 606 essentially appear as two dimensional pressure distributions.

In FIGS. 6A and 6B, the localized pressure produces a spike type response in one sensor. The pressure does not significantly affect the response of other sensors. In FIGS. 6C and 6D, however, sheath 300 distributes the localized pressure to adjacent or surrounding sensors. The distribution of the pressure may be characterized and measured by a width of distribution of that pressure ("W" in FIG. 6D). At the same time, sheath 300 reduces the peak pressure signal from the peak signal $P_1$ in FIG. 6B to $P_2$ in FIG. 6D.

Therefore, the effect of sheath 300 on the pressure signals may be characterized by two values: the amount or ratio by which sheath 300 reduces the peak value of the pressure signature and the amount or ratio by which sheath 300 increases the width of the pressure signature. To function effectively, sheath 300 should reduce the peak signal value P and increase distribution width W beyond selected minimum ratios or percentage values. For some applications, the ratios or percentage values should not exceed selected maximum values, either. For device 10, preferably, the minimum percentage value of change for both P and W is 2% and maximum percentage value of change is 15%.

The value of the change in the peak signal value P and distribution width W resulting from sheath 300 depends on the degree to which sheath 300 resists deflection. Sheath 300's degree of resistance to deflection in turn depends on the nature and the thickness of sheath 300 material. In order to determine the type and thickness of the material from which sheath 300 should be constructed to provide the desired change in the peak signal P and the distribution width W, we have developed a method of examining various material.

Figure 6E:
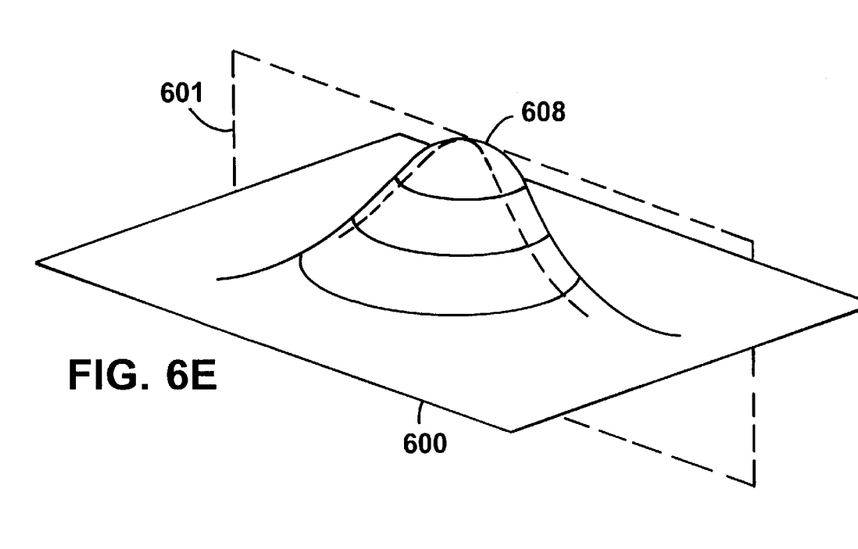
Figure 6F:
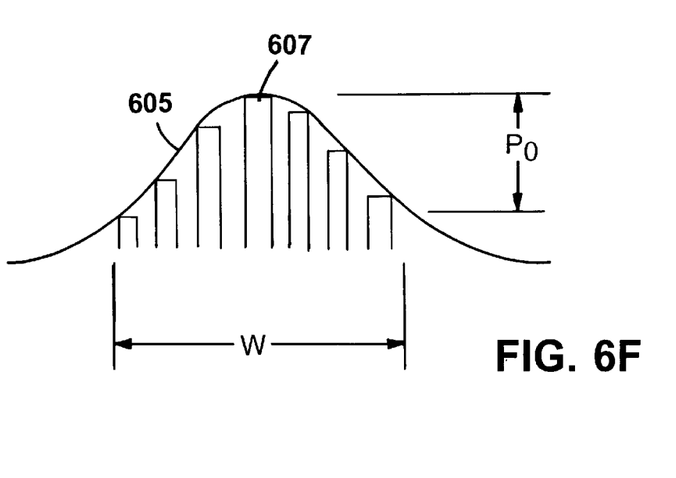

First, a standard load approximating a suspicious underlying structure is applied to array 104. FIG. 6E shows a three dimensional image 608 of the signals generated by array 104 in response to such a load. FIG. 6F shows a cross-section of image 608 along plane 601 which is coincident with the peak value of the shape 608 and parallel with the direction in which array 104 is pressed into the tissue. The peak pressure value and the distribution width W of the response are then measured.

Second, a sheath constructed from the type and thickness of a material to be tested is placed over sensors 102 and the same standard load is applied again. The peak pressure and the distribution width W are measured once again. The percentage change in these values from the previous measurements are then calculated and compared to the desired range of values.

The choice of material to be selected for making sheath 300 may also be affected by other factors such as manufacturing concerns, biocompatibility, and choice of a lubricant that will work optimally with the material. For device 10, sheaths made out of 0.001–0.005"'" thick polyurethane are preferable. (Of course, other material are also acceptable.)

Sheath 300 may be constructed from polyurethane by a variety of methods. We have found that the process of vacuum forming thin sheets of polyurethane material over a male mold, using standard plastics processing techniques, produces acceptably constant thicknesses in lower portion 301. Another method of producing sheaths is dip-forming sheath 300, a method commonly used to manufacture prophylactic sheaths. This method is however more expensive than producing sheaths by vacuum forming them.

Having described one way in which sheath 300 distributes pressure away from sensors in array 104, we will now describe a second way in which sheath 300 distributes the pressure. That is, we will describe how sheath 300 transfers shear stress on array 104 to housing 50.

Figure 7:
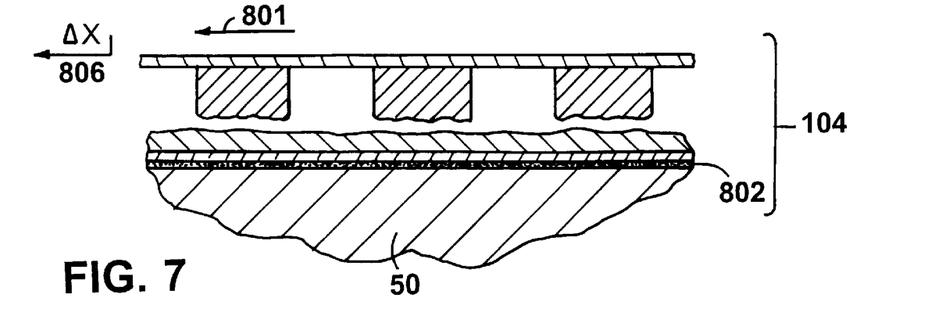

Referring to FIG. 7, as mentioned above, device 10 during operation is translated over tissue. Even if lubricant is used, a shear stress 801 is applied to top layer 403 of array 104 while bottom layer 404 is constrained by adhesive 802 that bonds array 104 to sensor head 202. The top and bottom layers of an array are thin and flexible and can move relative to one another when array 104 is in a flat state. Therefore, shear stress 801 will force top layer 403 to displace 806 relative to bottom layer 404, causing the FSR ink on the top and bottom layers to rub on one another. Since FSR ink is typically both abrasive and fragile, the rubbing of the two FSR ink layers on one another over time degrades the integrity of the FSR ink layers and reduces the sensitivity of sensors 102 to normal loads which device 10 needs to measure for proper operation.

Figure 8:
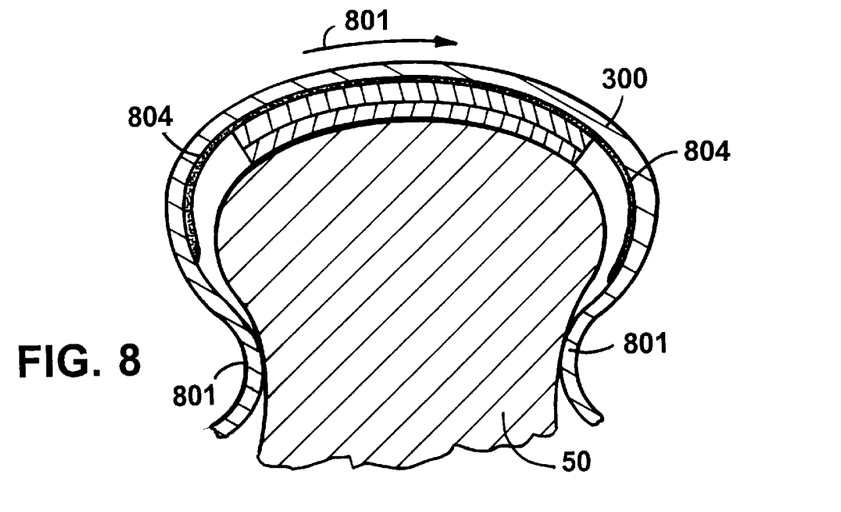
FIG. 8 show cross-sections of a sensor head, an array of pressure sensors and a sheath installed on the sensor head.

FIG. 8 shows a cross-section of sheath 300 installed on sensor head 202. When viewed along its cross-section, as in FIG. 8, sheath 300 appears as a cord that is fixed at its two ends 801 to housing 50 by friction and is in loose contact with the sensor surface. When a shear stress 801 is applied to sheath 300, the shear stress is transferred to housing 50 since sheath 300 does not stretch and does not move relative to the sensor head. Relative motion between the layers of array 104 can occur only if two conditions are met: first, the shear stress is strong enough to stretch sheath 300 or to overcome the friction between sheath 300 and housing 50 at sheath end 801 and move sheath 300 relative to the sensor head; and, second, the friction between sheath 300 and top layer 403 is large enough so that moving sheath 300 moves top layer 403 of the sensor. The loads encountered by device 10 in normal use are not typically great enough to stretch sheath 300 or to overcome the friction at sheath end 801. Moreover, a dry lubricant 804 between top layer 403 of the sensor and sheath 300 reduces the friction between array 104 and sheath 300. Therefore, even if sheath 300 is stretched or removed, sheath 300 can easily slide across array 104 because of the reduced friction.

Moreover, the material from which sheath 300 is made of can be selected based on whether it interacts well with a lubricant or a group of lubricants to be applied to the tissue to be examined such that the combination of the selected material and lubricant (or lubricants) enhance the degree of lubrication. Therefore, the shear stress can be further reduced by selecting appropriate sheath material and lubricant (or lubricants). In the case of not using a sheath, since there is typically less freedom, if any, in selecting top layer 403 of sensors 102, the degree of lubrication can typically not be enhanced by changing top layer 403 of sensors 102.

Other embodiments are within the scope of the following claims.

Figure 9:
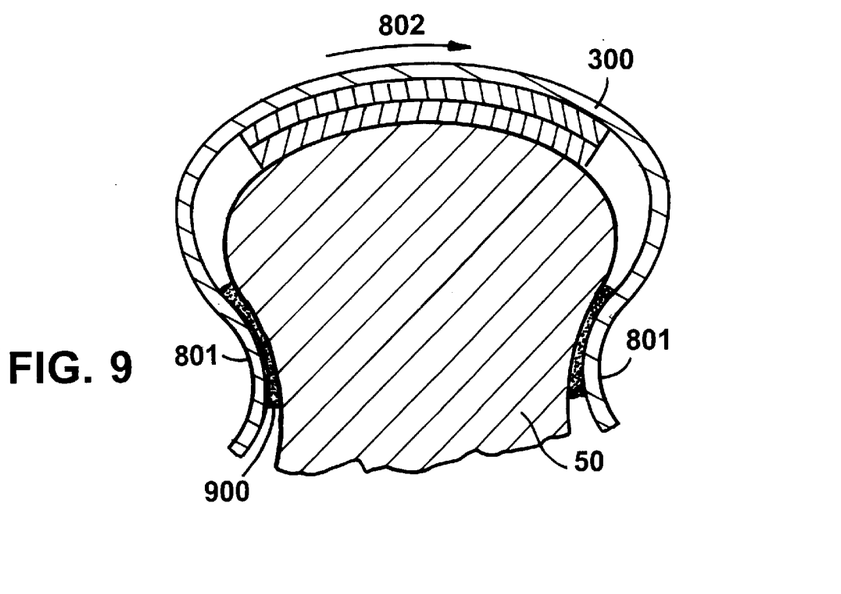
FIG. 9 shows a cross-section of a sensor head, an array of pressure sensors and a sheath installed on the sensor head.

For example, referring to FIG. 9, sheath 300 may be permanently attached to neck 216 by adhesive 900.

As mentioned above, FIG. 10 shows embodiment 20 of device 10 in accordance with the '573 application. Sheath 300 may also be used with device 20. Embodiment 20 includes a sensor head 22 and a console 24. Console 24 houses the circuitry to be used for the operation including a preprocessing circuit and a processor (not shown). Console 24 also includes a printer 28 and a visual display 26 for displaying to a user three-dimensional images of the pressure signature and other displays in accordance with the '573 application.

What is claimed is:

1. Apparatus comprising
   a tissue examination device that includes a plurality of pressure sensors that produce signals in response to pressure imposed thereon as the sensors are pressed against tissue, a housing having a distal region defining a maximum dimension, the pressure sensors being disposed on said distal region of the housing, and a processor for processing said signals to detect whether an underlying tissue structure is present in the tissue being examined, and
   a layer of material comprising
      a sensor covering portion configured to be disposed over the sensors and to distribute the imposed pressure in a selected manner, and
      an attachment portion extending the sensor covering portion to define a cavity for receiving the distal region of the housing, said attachment portion being smaller than the maximum dimension defined by the distal region of the housing and being flexible so that the attachment portion can be stretched over the distal region of the housing when the distal region is inserted into the cavity and tends to return to its original size to cause the attachment portion to engage against the housing.

2. The apparatus of claim 1 wherein the sensor covering portion distributes pressure imposed on a sensor to an adjacent sensor.

3. The apparatus of claim 2 wherein the sensor covering portion distributes the pressure imposed on the sensor to surrounding sensors.

4. The apparatus of claim 2, wherein the sensors have a top layer and the sensor covering portion is configured to reduce a deflection of the top layer in response to the imposed pressure.

5. The apparatus of claim 1 wherein the imposed pressure comprises shear stress imposed by the tissue on the sensors when the sensors are moved over the tissue and the sensor covering portion distributes the shear stress to reduce the shear stress imposed on the sensors.

6. The apparatus of claim 5 wherein the sensors have a top and a bottom layer, the top layer being capable of moving relative to the bottom layer in response to the shear stress, wherein the sensor covering portion is configured to reduce a movement of the top layer relative to the bottom layer caused by the shear stress.

7. The apparatus of claim 6 further comprising a lubricant between the top layer of the sensors and the sensor covering portion.

8. The apparatus of claim 5 wherein the sensor covering portion is configured to distribute the shear stress imposed on the sensor covering portion to the housing of the tissue examination device through the attachment portion to reduce the shear stress on the sensors.

9. The apparatus of claim 1 wherein the housing further comprises a neck connected to the distal region of the housing and the attachment portion is configured to frictionally engage the neck.

10. The apparatus of claim 1 wherein the housing further comprises a neck connected to the distal region and the attachment portion adhesively attaches to the neck.

11. The apparatus of claim 1 wherein the layer of material is constructed from a material selected for distributing pressure imposed on one of the sensors to surrounding sensors.

12. The apparatus of claim 11, wherein the layer of material is constructed from polyurethane.

13. The apparatus of claim 12, wherein the polyurethane has a thickness of 0.001–0.005 inch.

14. The apparatus of claim 1 wherein the layer of material is constructed from a material selected for operating with a selected lubricant.

15. A layer of material for a tissue examination device that includes a plurality of pressure sensors that produce signals in response to pressure imposed thereon as the sensors are pressed against tissue, a housing having a distal region defining a maximum dimension, the pressure sensors being disposed on said distal region of the housing, and a processor for processing said signals to detect whether an underlying tissue structure is present in the tissue being examined, the layer of material comprising a sensor covering portion configured to be disposed over the sensors and to distribute the imposed pressure in a selected manner, and an attachment portion extending from the sensor covering portion to define a cavity for receiving the distal region of the housing, said attachment portion being smaller than the maximum dimension defined by the distal region of the housing and being flexible so that the attachment portion can be stretched over the distal region of the housing when the distal region is inserted into the cavity and tends to return to its original size to cause the attachment portion to engage against the housing.

16. The layer of material of claim 15, wherein the sensor covering portion, when disposed over the sensors of the tissue examination device, distributes pressure imposed on a sensor to an adjacent sensor.

17. The layer of material of claim 16, wherein the sensor covering portion, when disposed over the sensors of the tissue examination device, distributes the pressure imposed on the sensor to surrounding sensors.

18. The layer of material of claim 17, wherein the sensors have a top layer and the sensor covering portion, when disposed over the sensors of the tissue examination device, is configured to reduce a deflection of the top layer in response to the imposed pressure.

19. The layer of material of claim 16, wherein the imposed pressure comprises shear stress imposed by the tissue on the sensors when the sensors are moved over the tissue and the sensor covering portion, when disposed over the sensors of the tissue examination device, distributes the shear stress to reduce the shear stress imposed on the sensors.

20. The layer of material of claim 19, the sensors have a top and a bottom layer, the top layer being capable of moving relative to the bottom layer in response to the shear stress, wherein the sensor covering portion is configured to reduce a movement of the top layer relative to the bottom layer caused by the shear stress, when the sensor covering portion is disposed over the sensors of the tissue examination device.

21. The layer of material of claim 19, wherein the sensor covering portion is configured so that, when disposed over the sensors of the tissue examination device, the sensor covering portion distributes the shear stress imposed on the sensor covering portion to the housing of the tissue examination device through the attachment portion to reduce the shear stress on the sensors.

22. The layer of material of claim 15, wherein the housing further comprises a neck connected to the distal region of the housing, and the attachment portion is configured to frictionally engage the neck.

23. The layer of material of claim 15, wherein the layer of material is constructed from a material selected for distributing pressure imposed on one of the sensors to surrounding sensors, when the sensor covering portion is disposed over the sensors of the tissue examination device.

24. The layer of material of claim 15, wherein the layer of material is constructed from a material selected for operating with a selected lubricant.

25. Apparatus comprising a tissue examination device that includes a plurality of pressure sensors that produce signals in response to pressure imposed thereon as the sensors are pressed against tissue, and a housing having a distal region defining a maximum dimension, the pressure sensors being disposed on said distal region or the housing, and a layer of material comprising a sensor covering portion configured to be disposed over the sensors and to distribute the imposed pressure in a selected manner, and an attachment portion extending from the sensor covering portion to define a cavity for receiving the distal region of the housing, said attachment portion being smaller than the maximum dimension defined by the distal region of the housing and being flexible so that the attachment portion can be stretched over the distal region of the housing when the distal region is inserted into the cavity.

26. The apparatus of claim 25, wherein the tissue examination device further comprises a processor for processing the signals generated by the sensors to generate an image representative of the underlying tissue structure, and a display for displaying said image.

27. The apparatus of claim 25, wherein the sensor covering portion distributes pressure imposed on a sensor to an adjacent sensor.

28. The apparatus of claim 27, wherein the sensors have a top layer and the sensor covering portion is configured to reduce a deflection of the top layer in response to the imposed pressure.

29. The apparatus of claim 28, wherein the imposed pressure comprises shear stress imposed by the tissue on the sensors when the sensors are moved over the tissue and the sensor covering portion distributes the shear stress to reduce the shear stress imposed on the sensors.

30. The apparatus of claim 29, wherein the sensor covering portion is configured to distribute the shear stress imposed on the sensors to the housing of the tissue examination device through the attachment portion to reduce the shear stress.

31. A layer of material for a tissue examination device that includes a plurality of pressure sensors that produce signals in response to pressure imposed thereon as the sensors are pressed against tissue, and a housing having a distal region defining a maximum dimension, the pressure sensors being disposed on said distal region of the housing, the layer of material comprising a sensor covering portion configured to be disposed over the sensors and to distribute the imposed pressure in a selected manner, and an attachment portion extending from the sensor covering portion to define a cavity for receiving the distal region of the housing, said attachment portion being smaller than the maximum dimension defined by the distal region of the housing, and being flexible so that the attachment portion can be stretched over the distal region of the housing when the distal region is inserted into the cavity and tends to return to its original size to cause the attachment portion to engage against the housing.

32. The layer of material of claim 31, wherein the sensor covering portion, when disposed over the sensors of the tissue examination device, distributes pressure imposed on a sensor to surrounding sensors.

33. The layer of material of claim 32, wherein the sensors have a top layer and the sensor covering portion is configured to reduce a deflection of the top layer in response to the imposed pressure, when the sensor covering portion is disposed over the sensors of the tissue examination device.

34. The layer of material of claim 31, wherein the imposed pressure comprises shear stress imposed by the tissue on the sensors when the sensors are moved over the tissue and the sensor covering portion, when disposed over the sensors of the tissue examination device, distributes the shear stress to reduce the shear stress imposed on the sensors.

35. The layer of material of claim 34, wherein the sensor covering portion, when disposed over the sensors of the tissue examination device, distributes pressure imposed on a sensor to the housing of the tissue examination device through the attachment portion to reduce the shear stress.

36. A method for examining tissue comprising providing a tissue examination device that includes a plurality of pressure sensors that produce signals in response to pressure imposed thereon as the sensors are pressed against tissue, and a housing having a distal region defining a maximum dimension, the pressure sensors being disposed on said distal region of the housing, providing a layer of material that comprises a sensor covering portion, and a flexible attachment portion extending from the sensor covering portion to define a cavity for receiving the distal region of the housing, said attachment portion being smaller than the maximum dimension defined by the distal region of the housing, inserting the distal region of the housing into the cavity and stretching the attachment portion over the distal region of the housing so that the attachment portion tends to return to its original size to cause the attachment portion to engage against the housing with the sensor covering portion being disposed over the sensors to distribute the imposed pressure in a selected manner, and pressing the sensors against the tissue to examine the tissue.

37. The apparatus of claim 1 wherein the attachment portion is sized such that the attachment portion remains in an at least partially stretched condition when engaged against the distal region of the housing.

38. The apparatus of claim 1 wherein the sensor covering portion is sized smaller than the distal region of the housing and is flexible such that the sensor covering portion is disposed over the sensors in at least a partially stretched condition.

39. The apparatus of claim 1 wherein the distal region of the housing is characterized by a general contour, the sensor covering portion being configured to substantially follow the general contour when attached to the housing.

40. The apparatus of claim 9 wherein the attachment portion is sized smaller than the neck such that the attachment portion is in an at least partially stretched condition when engaged thereagainst.

41. The layer of material of claim 15, wherein the attachment portion is sized such that the attachment portion remains in an at least partially stretched condition when engaged against the distal region of the housing.

42. The layer of material of claim 15, wherein the sensor covering portion is sized smaller than the distal region of the housing and is flexible such that the sensor covering portion is disposed over the sensors in at least a partially stretched condition.

43. The layer of material of claim 15, wherein the distal region of the housing is characterized by a general contour, the sensor covering portion being configured to substantially follow the general contour when attached to the housing.

44. The layer of material of claim 22, wherein the attachment portion is sized smaller than the neck such that the attachment portion is in an at least partially stretched condition when engaged thereagainst.

45. The layer of material of claim 23, wherein the layer of material is constructed from polyurethane.

46. The layer of material of claim 45, wherein the polyurethane has a thickness of 0.001–0.005 inch.

47. The apparatus of claim 25, wherein the housing further comprises a neck connected to the distal region of the housing and the attachment portion is configured to frictionally engage the neck.

48. The apparatus of claim 47, wherein the attachment portion is sized smaller than the neck such that the attachment portion is in an at least partially stretched condition when engaged thereagainst.

49. The apparatus of claim 25, wherein the layer of material is constructed from a material selected for distributing pressure imposed on one of the sensors to surrounding sensors.

50. The apparatus of claim 49, wherein the layer of material is constructed from polyurethane.

51. The apparatus of claim 50, wherein the polyurethane has a thickness of 0.001–0.005 inch.

52. The apparatus of claim 25, wherein the layer of material is constructed from a material selected for operating with a selected lubricant.

53. The apparatus of claim 25, wherein the attachment portion is sized such that the attachment portion remains in an at least partially stretched condition when engaged against the distal region of the housing.

54. The apparatus of claim 25, wherein the sensor covering portion is sized smaller than the distal region of the housing and is flexible such that the sensor covering portion is disposed over the sensors in at least a partially stretched condition.

55. The apparatus of claim 25, wherein the distal region of the housing is characterized by a general contour, the sensor covering portion being configured to substantially follow the general contour when attached to the housing.

56. The layer of material of claim 31, wherein the housing of the tissue examination device further comprises a neck connected to the distal region of the housing and the attachment portion is configured to frictionally engage the neck.

57. The layer of material of claim 56, wherein the attachment portion is sized smaller than the neck such that the attachment portion is in an at least partially stretched condition when engaged thereagainst.

58. The layer of material of claim 31, wherein the layer of material is constructed from a material selected for distributing pressure imposed on one of the sensors to surrounding sensors, when the sensor covering portion is disposed over the sensors of the tissue examination device.

59. The layer of material of claim 58, wherein the layer of material is constructed from polyurethane.

60. The layer of material of claim 59, wherein the polyurethane has a thickness of 0.001–0.005 inch.

61. The layer of material of claim 31, wherein the layer of material is constructed from a material selected for operating with a selected lubricant.

62. The layer of material of claim 31, wherein the attachment portion is sized such that the attachment portion remains in an at least partially stretched condition when engaged against the distal region of the housing.

63. The layer of material of claim 31, wherein the sensor covering portion is sized smaller than the distal region of the housing and is flexible such that the sensor covering portion is disposed over the sensors in at least a partially stretched condition.

64. The layer of material of claim 31, wherein the distal region of the housing is characterized by a general contour, the sensor covering portion being configured to substantially follow the general contour when attached to the housing.

65. The method of claim 36, further comprising processing said signals to detect whether an underlying tissue structure is present in the tissue being examined.

66. The method of claim 36, further comprising processing said signals to generate an image representative of an underlying tissue structure, and displaying said image.

67. The method of claim 36, further comprising stretching the proximal end of the attachment portion over the distal region of the housing to remove the distal region of the housing from the cavity through the opening.

* * * * *

UNITED STATES PATENT AND TRADEMARK OFFICE
CERTIFICATE OF CORRECTION

PATENT NO. : 6,179,790 B1  Page 1 of 1
DATED : January 30, 2001
INVENTOR(S) : Michael A. Cundari, Troy W. Roberts and Alan I. West It is certified that error appears in the above-identified patent and that said Letters Patent is hereby corrected as shown below:

Column 4,
Line 9, replace "A-A''" with -- A-A' --

Column 5,
Line 45, replace "122a-122i" with -- 122a-122n -- (both occurrences).
Line 48, replace "122a-122i" with -- 122a-122n -- .
Line 52, replace "122a-122i" with -- 122a-122n --.

Column 6,
Line 44, replace "122a-122i" with -- 122a-122n --.

Column 11,
Line 24, replace "0.001-0.005''''" with -- 0.001-005 --.

Column 12, claim 1,
Line 52, after "extending" insert -- from --.

Signed and Sealed this

Twentieth Day of November, 2001

Attest:

*Nicholas P. Godici*

*Attesting Officer*

NICHOLAS P. GODICI
*Acting Director of the United States Patent and Trademark Office*